US012634210B2

(12) United States Patent
Trapani et al.

(10) Patent No.: US 12,634,210 B2
(45) **Date of Patent: \*May 19, 2026**

(54) SYSTEMS AND METHODS FOR MONITORING INTER-APPLICATION COMMUNICATIONS IN COMPLEX COMPUTING ECOSYSTEMS

(71) Applicant: Express Scripts Strategic Development, Inc., St. Louis, MO (US)

(72) Inventors: Michael D. Trapani, Victor, NY (US); Scott H. Reid, Lynbrook, NY (US); Jason T. Graklanoff, Edwardsville, IL (US); Matthew M. Heck, St. Peters, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 148 days.

This patent is subject to a terminal disclaimer.

(21) Appl. No.: 18/534,914

(22) Filed: Dec. 11, 2023

(65) Prior Publication Data

US 2024/0113949 A1    Apr. 4, 2024

Related U.S. Application Data

(63) Continuation of application No. 17/867,118, filed on Jul. 18, 2022, now Pat. No. 11,848,834, which is a
(Continued)

(51) Int. Cl.
H04L 43/04      (2022.01)
G06F 9/54       (2006.01)
(Continued)

(52) U.S. Cl.
CPC ............. *H04L 43/04* (2013.01); *G16H 20/10* (2018.01); *H04L 43/08* (2013.01); *G06F 9/54* (2013.01)

(58) Field of Classification Search
CPC ......... H04L 43/10; H04L 43/16; H04L 41/12; H04L 41/22; H04L 41/0893; G16H 20/10; G16H 40/20; G06F 9/54
(Continued)

(56) References Cited

U.S. PATENT DOCUMENTS 7,543,128 B2 * 6/2009 Woods ................. G06F 3/0605
                                                                711/170
8,577,718 B2 * 11/2013 Wolf ............... G06Q 10/06395
                                                                705/7.41
(Continued)

*Primary Examiner* — James N Fiorillo
(74) *Attorney, Agent, or Firm* — Stinson LLP

(57) ABSTRACT

A monitoring system for mapping and monitoring inter-application communications in a computing ecosystem is described. The monitoring system provides consolidated visibility to computing ecosystems by providing end-to-end mapping and monitoring of inter-application communications and events, changes, incidents, and status information of applications, services, and systems. As described, the monitoring system is configured to (a) identify communication paths linking the host devices, (b) generate an ecosystem map based on the communication paths, (c) transmit a monitoring signal to the network, (d) receive a monitoring response from the host devices in response to the monitoring signal including at least a first status, (e) process the monitoring response with the ecosystem map to generate an active ecosystem map, and (f) display the active ecosystem map including the host devices and at least one status associated with the host devices. As such, the monitoring system provides consolidated visibility to the ecosystem.

20 Claims, 7 Drawing Sheets

Related U.S. Application Data continuation of application No. 16/527,239, filed on Jul. 31, 2019, now Pat. No. 11,394,627.

(51) Int. Cl.
  *G16H 20/10*   (2018.01)
  *H04L 43/08*   (2022.01)

(58) Field of Classification Search
  USPC ........................................................ 709/223
  See application file for complete search history.

(56)      References Cited

U.S. PATENT DOCUMENTS

| | | | | |
|---|---|---|---|---|
| 8,868,753 | B2 * | 10/2014 | Luna | H04L 47/70 709/224 |
| 9,761,119 | B1 * | 9/2017 | Trundle | G08B 29/16 |
| 9,836,527 | B2 * | 12/2017 | Gao | G06F 16/3329 |
| 10,142,164 | B2 * | 11/2018 | Ramachandran | H04L 45/28 |
| 10,158,545 | B1 * | 12/2018 | Marrone | H04L 41/0894 |
| 10,756,990 | B1 * | 8/2020 | Chakkassery Vidyadharan | G06F 11/301 |
| 10,778,659 | B2 * | 9/2020 | Tola | H04L 9/14 |
| 11,140,033 | B2 * | 10/2021 | Maria | H04L 41/145 |
| 11,159,389 | B1 * | 10/2021 | Miriyala | G06F 3/0484 |
| 11,238,380 | B1 * | 2/2022 | Perry | G06F 3/14 |
| 2003/0217212 | A1 * | 11/2003 | Kim | H04L 41/12 710/305 |
| 2007/0043767 | A1 * | 2/2007 | Osborne | G16H 10/60 |
| 2009/0006344 | A1 * | 1/2009 | Platt | G06F 16/90332 |
| 2010/0082822 | A1 * | 4/2010 | Yamazaki | H04L 45/00 709/228 |
| 2014/0089040 | A1 * | 3/2014 | Nandan | G06Q 30/016 705/7.28 |
| 2015/0066689 | A1 * | 3/2015 | Astore | G06Q 50/01 705/26.8 |
| 2015/0230022 | A1 * | 8/2015 | Sakai | H04R 1/1041 381/58 |
| 2016/0034668 | A1 * | 2/2016 | Rourke | G06Q 10/06315 705/2 |
| 2016/0125414 | A1 * | 5/2016 | Desai | G06Q 20/10 705/17 |
| 2016/0253078 | A1 * | 9/2016 | Ebtekar | G06T 11/60 715/735 |
| 2018/0152313 | A1 * | 5/2018 | Jennequin | G06F 15/16 |
| 2018/0219743 | A1 * | 8/2018 | Garcia | H04L 41/0213 |
| 2018/0285840 | A1 * | 10/2018 | Hasan | G06Q 50/01 |
| 2018/0343567 | A1 * | 11/2018 | Ashrafi | H04L 67/10 |
| 2019/0096522 | A1 * | 3/2019 | Scriber | H04L 9/3247 |
| 2019/0207822 | A1 * | 7/2019 | Di Pietro | G06N 20/00 |
| 2020/0117757 | A1 * | 4/2020 | Yanamandra | G06F 16/254 |
| 2020/0162337 | A1 * | 5/2020 | Jain | H04L 43/08 |
| 2020/0162994 | A1 * | 5/2020 | Jayawardena | H04W 40/02 |
| 2021/0210185 | A1 * | 7/2021 | Allred | G16H 20/10 |
| 2023/0015677 | A1 * | 1/2023 | Mahesh | H04L 43/16 |

* cited by examiner

Pallet Sizing And Pucking Device(s) — 206

Loading Device(s) — 208

Inspect Device(s) — 210

Unit of Use Device(s) — 212

Automated Dispensing Device(s) — 214

Manual Fulfillment Device(s) — 216

Review Devices — 218

Imaging Device(s) — 220

Cap Device(s) — 222

Accumulation Devices — 224

Packing Device(s) — 226

Literature Device(s) — 228

Unit of Use Packing Device(s) — 230

Mail Manifest Device(s) — 232

112

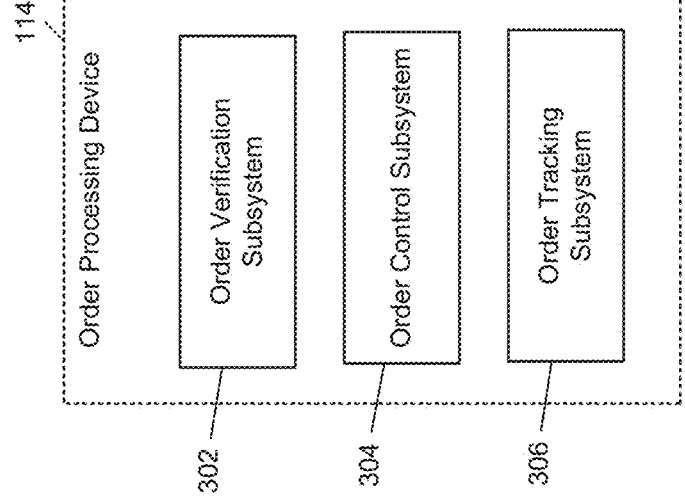
FIG. 3

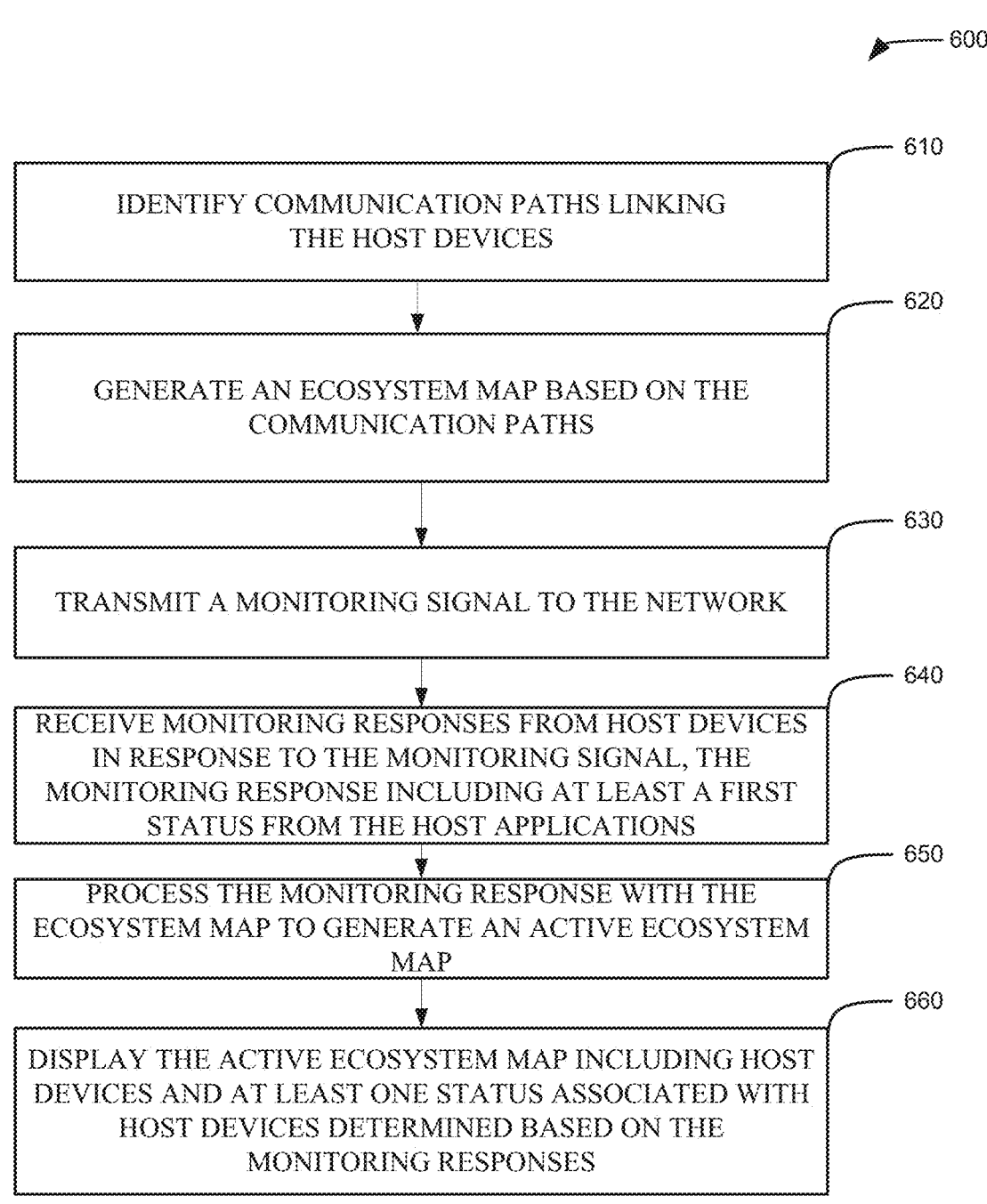

600

610

IDENTIFY COMMUNICATION PATHS LINKING
THE HOST DEVICES

620

GENERATE AN ECOSYSTEM MAP BASED ON THE
COMMUNICATION PATHS

630

TRANSMIT A MONITORING SIGNAL TO THE NETWORK

640

RECEIVE MONITORING RESPONSES FROM HOST DEVICES
IN RESPONSE TO THE MONITORING SIGNAL, THE
MONITORING RESPONSE INCLUDING AT LEAST A FIRST
STATUS FROM THE HOST APPLICATIONS

650

PROCESS THE MONITORING RESPONSE WITH THE
ECOSYSTEM MAP TO GENERATE AN ACTIVE ECOSYSTEM
MAP

660

DISPLAY THE ACTIVE ECOSYSTEM MAP INCLUDING HOST
DEVICES AND AT LEAST ONE STATUS ASSOCIATED WITH
HOST DEVICES DETERMINED BASED ON THE
MONITORING RESPONSES

FIG. 6

SYSTEMS AND METHODS FOR MONITORING INTER-APPLICATION COMMUNICATIONS IN COMPLEX COMPUTING ECOSYSTEMS

CROSS REFERENCE TO RELATED APPLICATIONS

This application is a continuation of U.S. application Ser. No. 17/867,118, filed Jul. 18, 2022, which is a continuation of U.S. application Ser. No. 16/527,239, filed Jul. 31, 2019 (now U.S. Pat. No. 11,394,627). The entire disclosures of said applications are incorporated herein by reference.

FIELD OF INVENTION

The field relates to tracking, monitoring, and mapping communications between applications in complex computing infrastructure to provide failure analysis and topological analysis tools.

BACKGROUND OF THE DISCLOSURE

In modern computing infrastructures, many distinct applications, services, and systems are often used within a particular environment or ecosystem. Further, in many such infrastructures, the applications, services, and systems provide disparate data sets, often in varying formats and structures. As a result, information provided by applications reflecting state and communication is often disparate across systems. Because of such disparate data, application information is often difficult to consolidate or review across systems.

Nevertheless, in complex ecosystems it is often most effective for applications to be reviewed in such a consolidated manner. In order to effectively manage complex ecosystems, administrators require consolidated views of the communications, events, changes, incidents, and status information of the applications, services, and systems.

Known systems and methods exist for diagramming and describing relationships within ecosystems. However, such systems and methods suffered from deficiencies of requiring manual updating and maintenance. Further, these systems and methods failed to include communications, events, changes, incidents, and status information of the applications, services, and systems, and instead principally functioned as a static map of an ecosystem. Other known systems provided limited discovery of events in ecosystems, but fail to provide implementations suitable for end-to-end mapping and monitoring of applications, services, and systems in an ecosystem.

Accordingly, systems and methods for providing consolidated visibility to computing ecosystems by providing end-to-end mapping and monitoring of inter-application communications and events, changes, incidents, and status information of applications, services, and systems.

BRIEF SUMMARY OF THE INVENTION

In one aspect, a monitoring system for mapping and monitoring inter-application communications in a computing ecosystem is provided. The monitoring system includes host devices including corresponding host processors and corresponding host memory devices. The host processor executes host applications. The monitoring system also includes a monitoring device including a processor and a memory device. The monitoring device is in networked communication with the host devices via a network. The processor is configured to (a) identify communication paths linking the host devices, (b) generate an ecosystem map based on the communication paths, (c) transmit a monitoring signal to the network, (d) receive monitoring responses from the host devices in response to the monitoring signal including at least a first status from the host applications, (e) process the monitoring response with the ecosystem map to generate an active ecosystem map, and (f) display the active ecosystem map including the host devices and at least one status associated with the host devices determined based on the monitoring responses.

In another aspect, a monitoring device including a processor and a memory device is provided. The monitoring device is in networked communication with host devices having corresponding host processors and corresponding host memory devices. The host processors execute host applications. The processor is configured to (a) identify communication paths linking the host devices, (b) generate an ecosystem map based on the communication paths, (c) transmit a monitoring signal to the network, (d) receive monitoring responses from the host devices in response to the monitoring signal including at least a first status from the host applications, (e) process the monitoring response with the ecosystem map to generate an active ecosystem map, and (f) and display the active ecosystem map including the host devices and at least one status associated with the host devices determined based on the monitoring responses.

In yet another aspect, a method is provided for mapping and monitoring inter-application communications in a computing ecosystem. The method is performed by a monitoring device including a processor and a memory device. The monitoring device is in networked communication with host devices having corresponding host processors and corresponding host memory devices. The host processors execute host applications. The method includes (a) identify communication paths linking the host devices, (b) generating an ecosystem map based on the communication paths, (c) transmitting a monitoring signal to the network, (d) receiving monitoring responses from the host devices in response to the monitoring signal including at least a first status from the host application, (e) processing the monitoring response with the ecosystem map to generate an active ecosystem map, and (f) displaying the active ecosystem map including the host device and at least one status associated with the host device determined based on the monitoring responses.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 3 is a functional block diagram of an example order processing device, which may be deployed within the system of FIG. 1.

FIG. 6 is a flow diagram representing a method for mapping and monitoring inter-application communications in a computing ecosystem performed by the monitoring device shown in FIG. 5.

DETAILED DESCRIPTION

Figure 1:
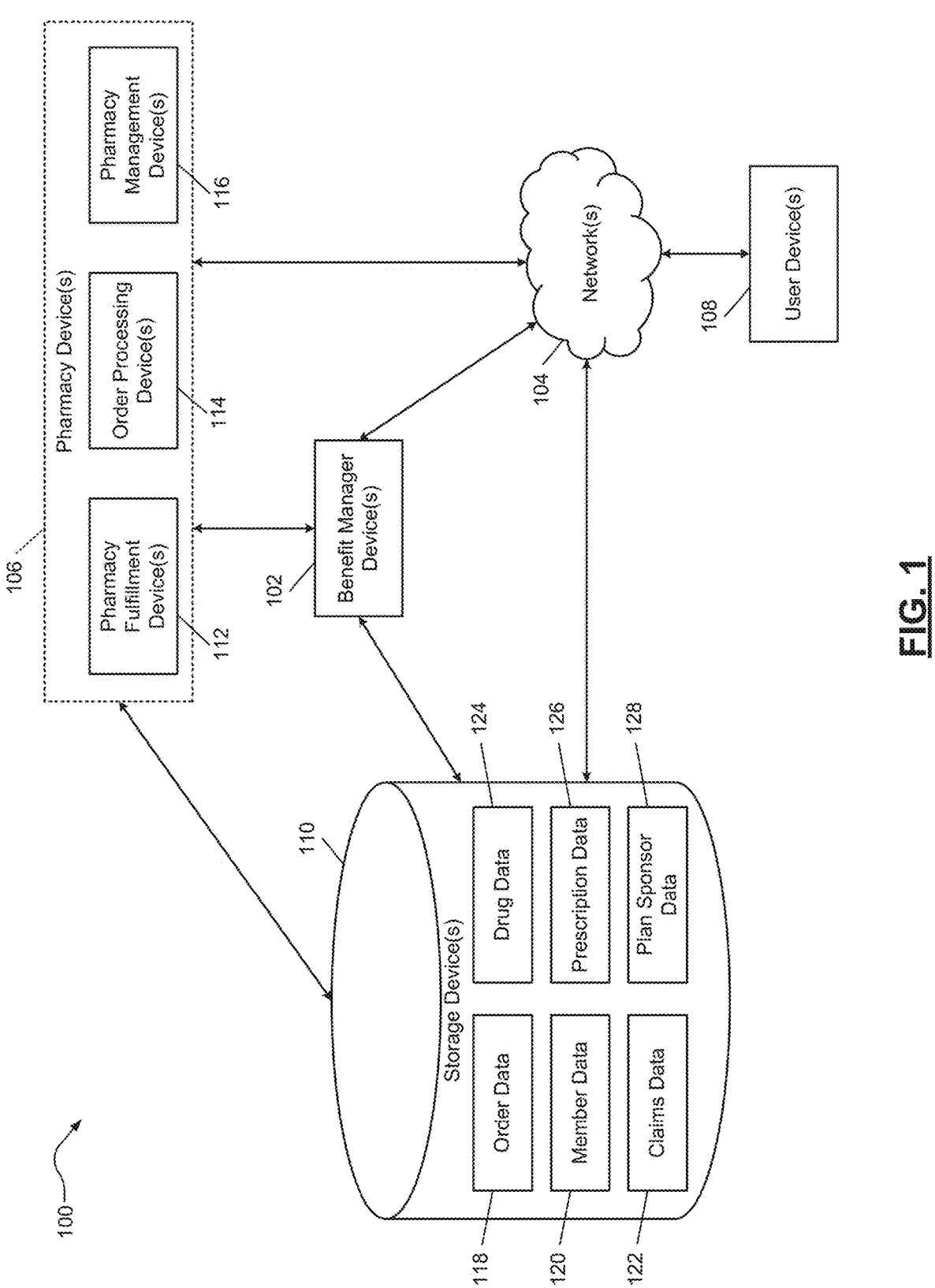
FIG. 1 is a functional block diagram of an example system including a high-volume pharmacy.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein, the term "single point of failure" or "SPOF" refers to a part of an information system that, if it fails, will cause a sub-system or an entire system to fail. Generally, it is undesirable for SPOFs to exist in any system or sub-system that has a requirement of high availability or reliability.

As used herein, the term "computing ecosystem" or "ecosystem" refers to a distributed computing system with a variety of systems, applications, software, and functions that are interconnected and provide collective functionality to one another and to external devices. An ecosystem may include computing systems that are tiered based on application category, grouped based upon service capabilities, or otherwise categorized based on a common set of characteristics.

In view of known problems associated with managing complex ecosystems, administrators require systems and methods for providing end-to-end mapping and monitoring of inter-application communications and events, changes, incidents, and status information of applications, services, and systems.

The systems and methods disclosed provide a comprehensive mechanism for such end-to-end mapping and monitoring of inter-application communications and events, changes, incidents, and status information of components of the ecosystem. Specifically, the systems and methods provide an end-to-end application communication flow capable of displaying overlaid and related contextual data about the ecosystem and sub-components of the ecosystem, including contextual data specific to logically determined clusters, service tiers, and other categorical groupings. Through such functionalities, the systems and methods effectively provide a central view (referred to as a "single pane of glass") for review and management of the ecosystem and subcomponents thereof. Further, in some embodiments, the systems and methods provide analytical tools for identifying SPOFs or points of failure based on, for example, a determination that a non-redundant system, application, host device, device, or other component supports a logical grouping and is therefore the only component in that logical grouping capable of providing a particular service. In additional embodiments, the systems and methods are configured to provide topological map tracing, highlighting, or other markups for demonstrating inter-component communications.

The systems and methods are performed by a monitoring device included within the computing ecosystem. In the example embodiment, the device is configured to be in communication with host devices having corresponding host processors and corresponding host memory devices. In some examples, each of the host devices have at least one host processor and at least one memory device. In other examples, some of the host devices may or may not have an associated host memory device or host processor because, for example, such host devices may use virtualization and utilize processors or memory available to multiple host devices, or because the host devices may not require an individual corresponding memory device or processor. The host processors execute host applications or provide services for other components in the ecosystem. In some examples, each host device is associated with a corresponding host application or a host service. The monitoring device includes a processor and a memory device.

The monitoring device is configured to (i) identify communication paths linking the host devices; (ii) generate an ecosystem map based on the communication paths; (iii) transmit a monitoring signal to the network; (iv) receive monitoring responses from the host devices in response to the monitoring signal, the monitoring response including at least a first status from the host applications; (v) process the monitoring response with the ecosystem map to generate an active ecosystem map; and (vi) display the active ecosystem map including the host devices and at least one status associated the each host devices determined based on the monitoring responses.

Further, the monitoring system is configured to execute a series of processes that collectively facilitate mapping and monitoring inter-application communications in a computing ecosystem. In particular, the processes include (a) providing an end-to-end view of inter-application communication flow, (b) providing overlaid and related contextual data about the ecosystem and sub-components of the ecosystem, including contextual data specific to logically determined clusters, service tiers, and other categorical groupings, (c) providing a single pane of glass for review and management of the ecosystem and subcomponents, (d) providing tools for identification of single points of failure, (e) and providing topology path highlighting and marking (sometimes referred to as "GPS").

In some examples, the systems and methods provided can be extended, adapted, or customized using application programming interfaces ("APIs") and libraries. In the example embodiment, the systems and methods utilize Java based APIs and libraries, but in alternative embodiments, any suitable programming language may be used. Further, the systems and methods described may be integrated with source systems that can provide information as a source or an update for the monitoring system.

The monitoring device is configured to identify communication paths linking the host devices. In the example embodiment, the communication paths are identified using an intermediary service that discovers and monitors communication paths between host devices. In another example, the monitoring device transmits an inquiry message to the network to identify assets within the ecosystem including the host devices, applications, and services. In most examples, the monitoring device uses any suitable method to identify communication paths linking the host devices including receiving the paths from an external service, from user input, or determining them through discovery. In one example, the inquiry message is received by each asset (or at least some assets) which responds with a response including at least an identifier sufficient to identify the asset. The identifier may include a network address, an asset name, a numerical asset identifier, or any other suitable designation. The response may also include asset characteristics, and organizational groupings of the asset (based on tier, cluster, service grouping, or any other suitable classification). In another example, the ecosystem includes an inventory device containing a data store that may store information regarding the ecosystem topology, including a listing of assets with associated identifiers and characteristics, and organizational groupings of the asset. In this example, when the monitoring device transmits the inquiry message to the network, the inventory device may provide the ecosystem topology information in response. In the example embodiment, the inventory device is a configuration management database ("CMDB") that is updated and validated regularly. In some examples, the response messages also include status information including changes to the asset, incidents and events, and asset health and status (including, for example, whether an asset is functional, non-functional, or experiencing performance issues).

The monitoring device also identifies communication paths linking the host devices. The communication paths describe the inter-asset communication in the ecosystem, and may be used to describe the ecosystem connectivity. In some examples, the monitoring device transmits the discovery message and the inquiry message simultaneously. In other examples, where the monitoring device identifies communication paths without the use of a discovery message, the monitoring device may identify the communication paths and send the inquiry message simultaneously.

In all embodiments, the monitoring device receives a response from at least one device in the ecosystem that is used to generate an ecosystem map based on the identified host devices provided in response to the inquiry message, and the identified communication paths. In some examples, the ecosystem map is re-generated and updated periodically and then stored for retrieval on-demand.

In some examples, the organizational grouping information may also be used to generate the map. For example, the monitoring device may group assets into logical groupings based on at least one of a host tier model and a host cluster model (or any other organizational model) and display the active ecosystem map such that the host devices are grouped by the logical groupings.

In further examples, the monitoring device is configured to generate the ecosystem map including multi-layered annotation. For example, the ecosystem map may be generated based upon a first level indicating topological ecosystem design, with additional levels including information associated with the assets. For example, the ecosystem map may include a secondary layer that provides contextual data related to each asset (or at least some assets) including, for example, asset identifiers, asset names, asset logical grouping information, asset tier, asset connectivity information, and asset characteristics. The ecosystem map may include a tertiary layer related to asset state including, for example, changes to the asset, incidents and events, and asset health and status (including, for example, whether an asset is functional, non-functional, or experiencing performance issues).

In some examples, the monitoring device is configured to group host devices into logical groupings based on a host cluster model and identify any non-redundant host device supporting at least one of the logical groupings. More specifically, based on the received communication paths and responses to inquiry messages, the monitoring device may determine that certain assets are non-redundant with any other assets, and therefore pose a risk of becoming a single point of failure for a service performed by the asset. The monitoring device is configured to make this determination by identifying assets that are not grouped with any other assets in a particular cluster for a particular service, and to annotate the ecosystem map by indicating that there is a risk of a single point of failure. In some examples, the monitoring device transmits an alert to a user or a secondary device indicating the single point of failure risk.

The monitoring device is also configured to transmit a monitoring signal to the network. The transmission of the monitoring signal may be scheduled on a periodic basis set by a user or a third-party system, or may be set based on a default for the ecosystem. In some examples, the monitoring device performs the monitoring indirectly. In such examples, the monitoring device transmits the monitoring signal to an external polling or monitoring service that actively polls the host devices. The monitoring device communicates with the external polling or monitoring service as an intermediary that contacts the host devices and then relays any received information back to the monitoring device. The monitoring device receives a monitoring response from the host devices in response to the monitoring signal. In the example embodiment, the monitoring response includes at least a first status from the assets, and more specifically from the host applications. In many examples, the monitoring response includes at least a first status from each asset, and each host application. In some examples, assets are unavailable or may fail to provide a monitoring response. In such examples, the monitoring device is configured to determine that a minimum wait threshold has passed and to determine that the first status was not provided for a particular asset. The monitoring device may attempt a retry of transmission of the monitoring signal. If the monitoring device fails to receive a response after a minimum amount of retries, the monitoring device may designate the non-responsive asset as unavailable or non-responsive. In such examples, the ecosystem map is updated to reflect the non-responsive or unavailable status, and the monitoring device may transmit an alert regarding the status. As noted, in some examples, the monitoring device receives a monitoring device from the host devices through an intermediary external polling or monitoring service.

The monitoring device is also configured to process the monitoring responses along with the ecosystem map to generate an active ecosystem map. The active ecosystem map reflects the topological map based on identified host devices and communication paths, along with at least some status information associated with the assets.

The monitoring device is configured to process such information by correlating data received in response to the inquiry message, the discovery request or identification of communication paths, and the monitoring signal and rationalizing data models between ecosystem layers such as the application and network layer.

The monitoring device is also configured to display the active ecosystem map including the host devices and at least one status associated with the host devices determined based on the monitoring responses. The active ecosystem map may be displayed on the monitoring device or on a device in communication therewith. In some examples, the active ecosystem map is updated regularly based on the frequency of monitoring signal transmission.

In further examples, the monitoring device is configured to provide an interactive tool for topological map tracing, highlighting, or other markups on the ecosystem map. In such examples, the monitoring device displays the active ecosystem map including a topological mapping tool that is configured to receive an input. Based on the input received at the topological mapping tool, the monitoring device determines an annotation or markup for the topological path indicated in the input and displays the active ecosystem map with a markup generated based on the input.

The systems and methods described address known pro managing complex ecosystems by providing end-to-end mapping and monitoring of inter-application communications. Notably, the systems and methods may be used to reduce mean time to resolution ("MTTR") of issues in an ecosystem.

Generally, the systems and methods described herein are configured to perform at least the following steps: (a) identify communication paths linking the host devices, (b) generate an ecosystem map based on the communication paths, (c) transmit a monitoring signal to the network, (d) receive monitoring responses from the host devices in response to the monitoring signal, the monitoring response including at least a first status from the host applications, (e) process the monitoring response with the ecosystem map to generate an active ecosystem map, (f) display the active ecosystem map including the host devices and at least one status associated the each host devices determined based on the monitoring responses, (g) identify the host devices by sending an inquiry message to the network, (h) generate an ecosystem map based on the identified host devices and the communication paths, (i) group host devices into logical groupings based on at least one of a host tier model and a host cluster model, (j) display the active ecosystem map, wherein the active ecosystem map displays the host devices grouped by the logical groupings, (k) display the active ecosystem map including a first layer representing a topological depiction of the host devices, and a second layer representing a set of information associated with the host devices, (l) group host devices into logical groupings based on a host cluster model, (m) identify a non-redundant host device supporting at least one of the logical groupings, (n) designate the non-redundant host device as a point-of-failure, (o) transmit an alert regarding the designated point-of-failure, (p) receive the monitoring response from the host devices, (q) perform a correlation between the monitoring responses to generate the active ecosystem map, (r) display the active ecosystem map including a topological mapping tool, (s) receive an input at the topological mapping tool, and (t) display the active ecosystem map with a first layer generated based on the input.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However, in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
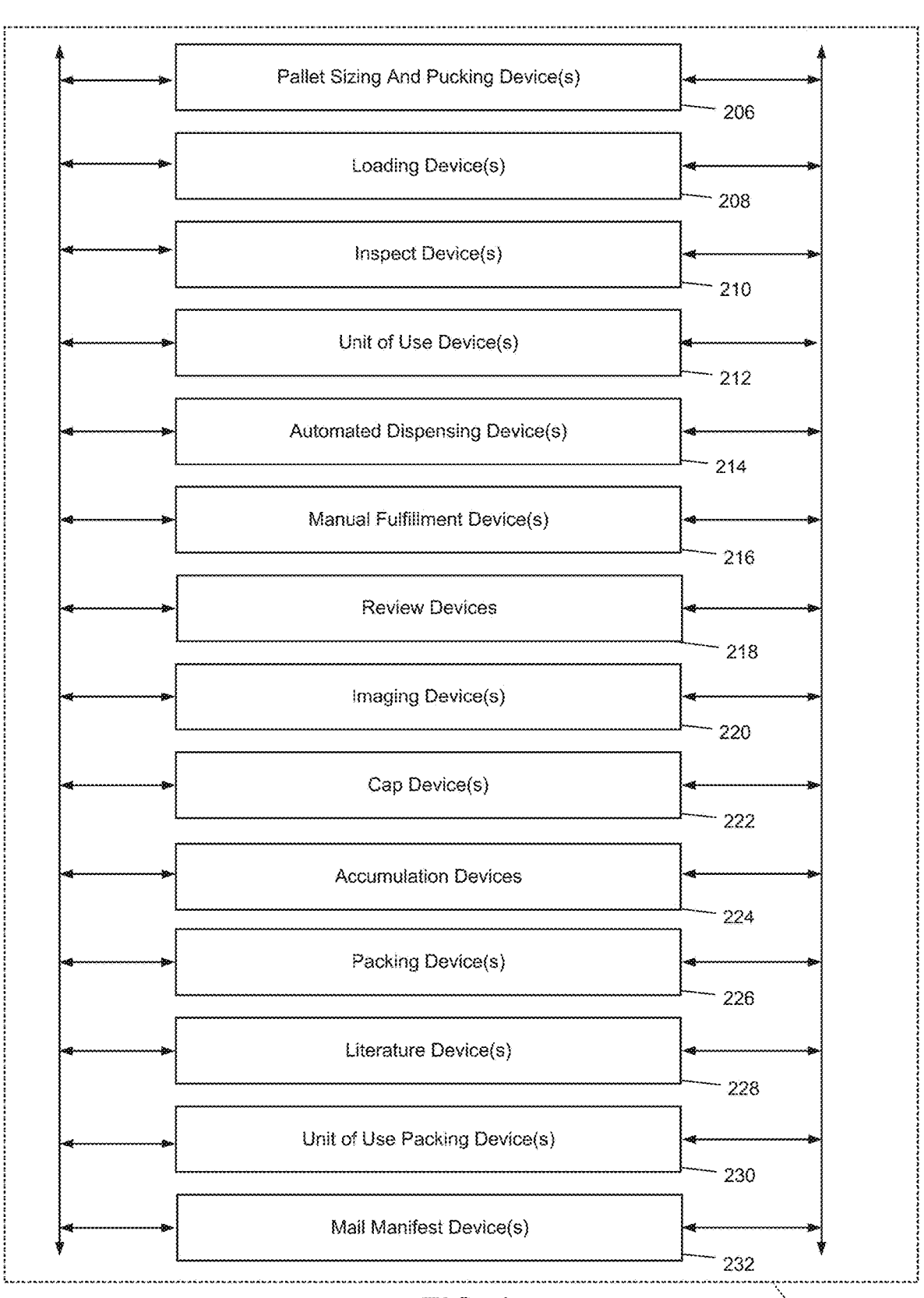
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container.

The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Figure 4:
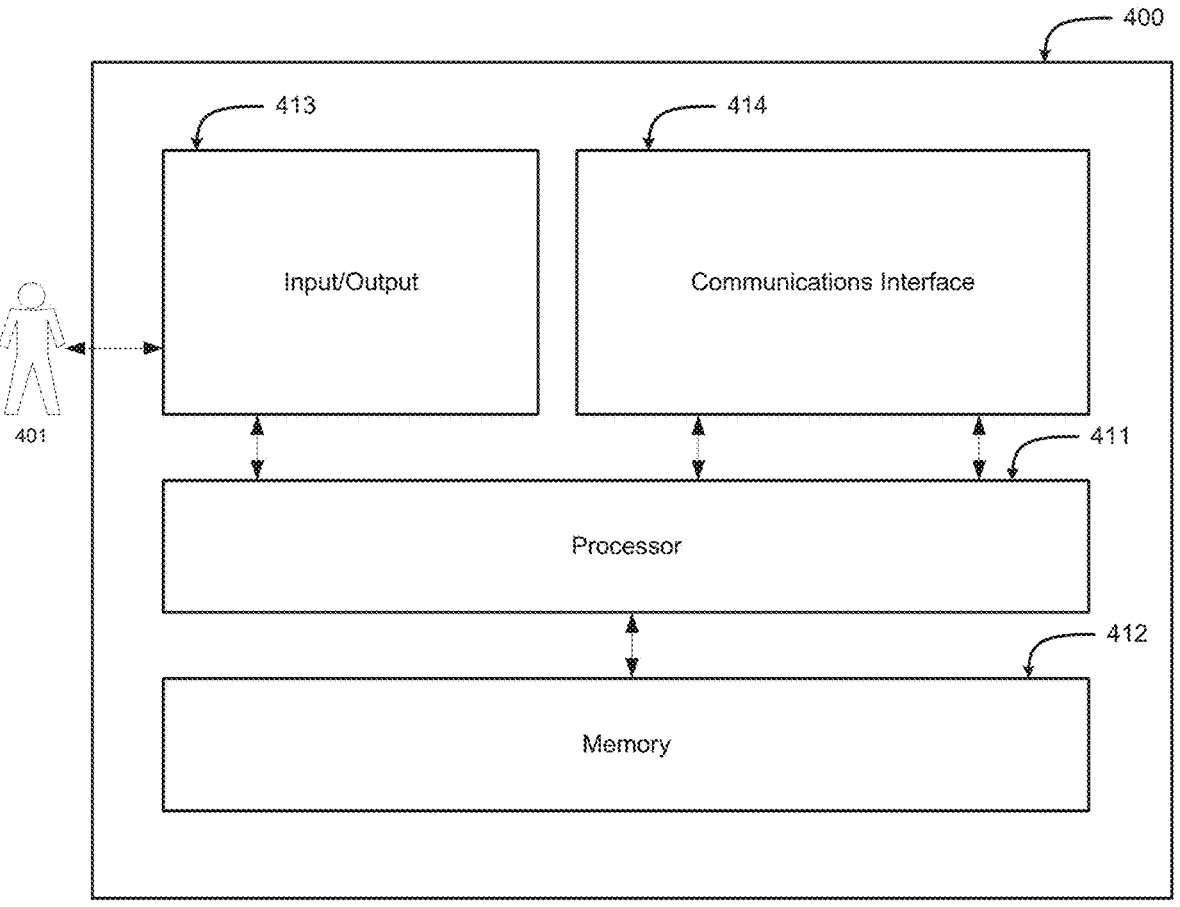
FIG. 4 is a functional block diagram of an example computing device that may be used in the environments described herein.

FIG. 4 is a functional block diagram of an example computing device 400 that may be used in the environments described herein. Specifically, computing device 400 illustrates an exemplary configuration of a computing device. Computing device 400 may be used to monitor inter-application communications in computing systems including system 100 (shown in FIG. 1) for high-volume pharmacies as well as any other suitable computing system. As such, computing device 400 may provide end-to-end mapping and monitoring of inter-application communications and events, changes, incidents, and status information of applications, services, and systems within, for example, devices 102, 106, 108, 110, 112, 114, and 116 as well as in other similar devices. Computing device 400 illustrates an exemplary configuration of a computing device operated by a user 401 in accordance with one embodiment of the present invention. Computing device 400 may include, but is not limited to, a monitoring device, a host device, an inventory device, and any other system described herein. Computing device 400 may also include pharmacy devices 106 including pharmacy fulfillment devices 112, order processing devices 114, and pharmacy management devices 116, storage devices 110, benefit manager devices 102, and user devices 108 (all shown in FIG. 1), mobile computing devices, stationary computing devices, computing peripheral devices, smart phones, wearable computing devices, medical computing devices, and vehicular computing devices. Alternatively, computing device 400 may be any computing device capable of performing the monitoring and mapping methods described herein. In some variations, the characteristics of the described components may be more or less advanced, primitive, or non-functional.

In the exemplary embodiment, computing device 400 includes a processor 411 for executing instructions. In some embodiments, executable instructions are stored in a memory area 412. Processor 411 may include one or more processing units, for example, a multi-core configuration. Memory area 412 is any device allowing information such as executable instructions and/or written works to be stored and retrieved. Memory area 412 may include one or more computer readable media.

Computing device 400 also includes at least one input/output component 413 for receiving information from and providing information to user 401. In some examples, input/output component 413 may be of limited functionality or non-functional as in the case of some wearable computing devices. In other examples, input/output component 413 is any component capable of conveying information to or receiving information from user 401. In some embodiments, input/output component 413 includes an output adapter such as a video adapter and/or an audio adapter. Input/output component 413 may alternatively include an output device such as a display device, a liquid crystal display (LCD), organic light emitting diode (OLED) display, or "electronic ink" display, or an audio output device, a speaker or headphones. Input/output component 413 may also include any devices, modules, or structures for receiving input from user 401. Input/output component 413 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 413. Input/output component 413 may further include multiple sub-components for carrying out input and output functions.

Computing device 400 may also include a communications interface 414, which may be communicatively couplable to a remote device such as a remote computing device, a remote server, or any other suitable system. Communication interface 414 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 414 is configured to allow computing device 400 to interface with any other computing device or network using an appropriate wireless or wired communications protocol such as, without limitation, BLUETOOTH®, Ethernet, or IEE 802.11. Communications interface 414 allows computing device 400 to communicate with any other computing devices with which it is in communication or connection.

Figure 5:
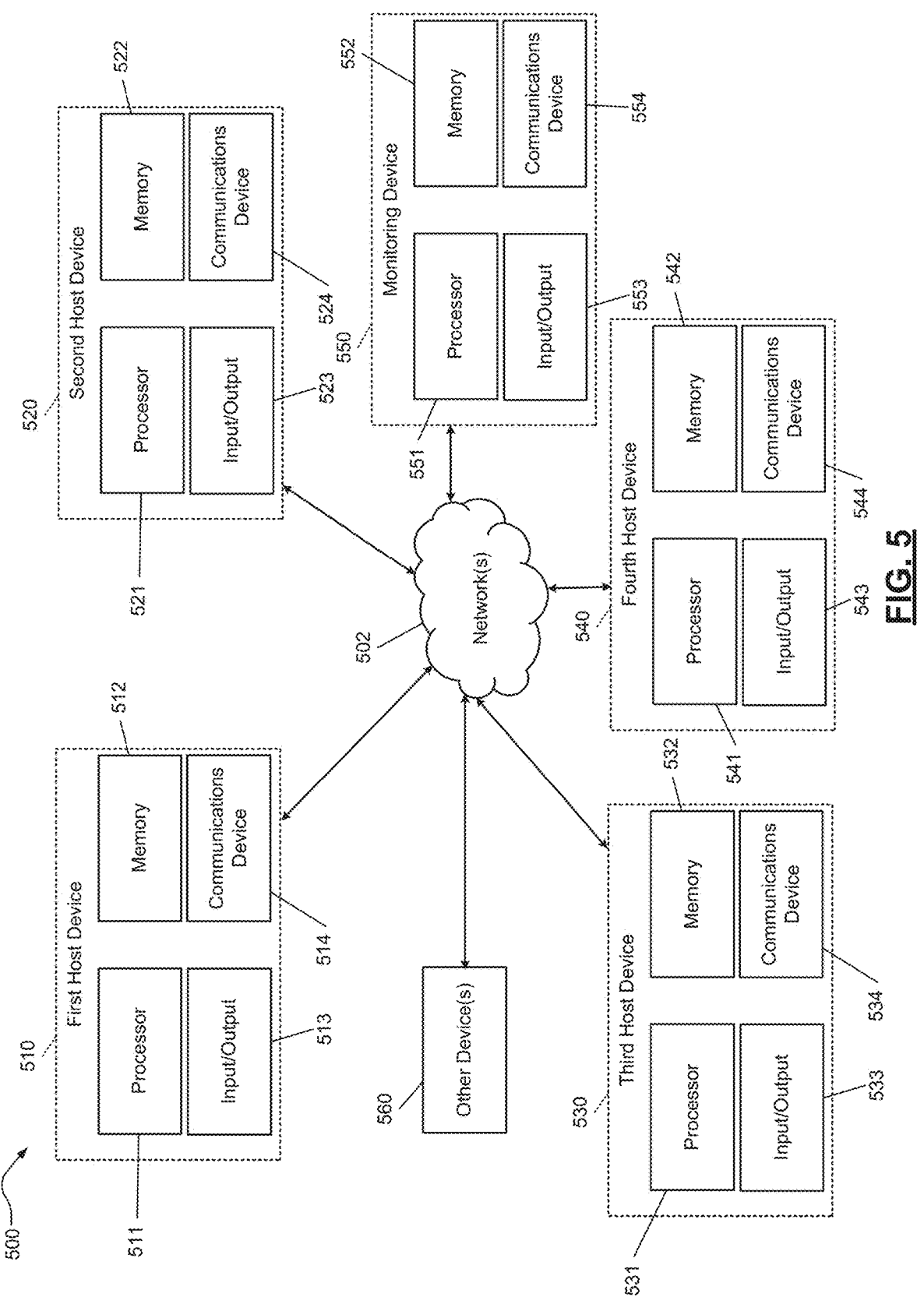
FIG. 5 is a functional block diagram of a monitoring system for mapping and monitoring inter-application communications in a computing ecosystem, including a monitoring device and multiple computing devices shown in FIG. 4.

FIG. 5 is a functional block diagram of a monitoring system 500 for monitoring an ecosystem, including multiple computing devices 510, 520, 530, 540, 550, and 560 similar to the computing device 400 shown in FIG. 4. As described above, computing device 400 may be used to monitor inter-application communications in computing systems including system 100 (shown in FIG. 1) for high-volume pharmacies as well as any other suitable computing system. As such, monitoring system 500 may include, or connect to, systems including system 100 and may be used to provide end-to-end mapping and monitoring of inter-application communications and events, changes, incidents, and status information of applications, services, and systems within, for example, devices 102, 106, 108, 110, 112, 114, and 116 as well as in other similar devices. Host devices 510, 520, 530, and 540 represent assets capable of providing services including applications to the ecosystem. In the example embodiment, each host device 510, 520, 530, and 540 includes a processor 511, 521, 531, and 541 a memory 512, 522, 532, and 542 an input/output 513, 523, 533, and 543 and a communications device 514, 524, 534, and 544. In some examples, some host devices 510, 520, 530, and 540 may not include all such elements because they may, for example, share processors, memory devices, input/output, communications devices, or other components with other host devices. In the example embodiment, each processor 511, 521, 531, and 541 is configured to provide at least one service or host application to the ecosystem. In some examples, the host devices 510, 520, 530, and 540 (and their associated processors, if any) may not provide a service or host application in each and every case. Monitoring device 550 is configured to facilitate or execute many of the processes described herein, and to coordinate the principal methods of mapping and monitoring inter-system communications within the ecosystem, and providing a "single pane of glass" view of the ecosystem, as well as to provide the functionality described herein. Monitoring device 550 includes a processor 551, a memory 552, an input/output 553, and a communications device 554. Other devices 560 may be designed in a manner similar to computing device 400 and similarly include processors, memories, input/ outputs, and communication devices. In some examples, other devices 560 includes an inventory device that hosts or has access to a configuration management database ("CMDB") that describes the assets in the ecosystem and their relationships. In some cases, the inventory device is distributed over multiple devices. Computing devices 510, 520, 530, 540, 550, and 560 are in networked communication via network 502.

FIG. 6 is a flow diagram representing a method 600 for mapping and monitoring inter-application communications in a computing ecosystem performed by the monitoring device 550 of the monitoring system 500 shown in FIG. 5. The monitoring device 550 is configured to identify 610 communication paths linking the host devices. The monitoring device 550 is also configured to generate 620 an ecosystem map based on the communication paths and to transmit 630 a monitoring signal to the network. The monitoring device 550 is additionally configured to receive 640 monitoring responses from the host devices in response to the monitoring signal, the monitoring response including at least a first status from the host application and to process 650 the monitoring response with the ecosystem map to generate an active ecosystem map. The monitoring device is also configured to display 660 the active ecosystem map including the host devices and at least one status associated with the host devices determined based on the monitoring responses.

Figure 7:
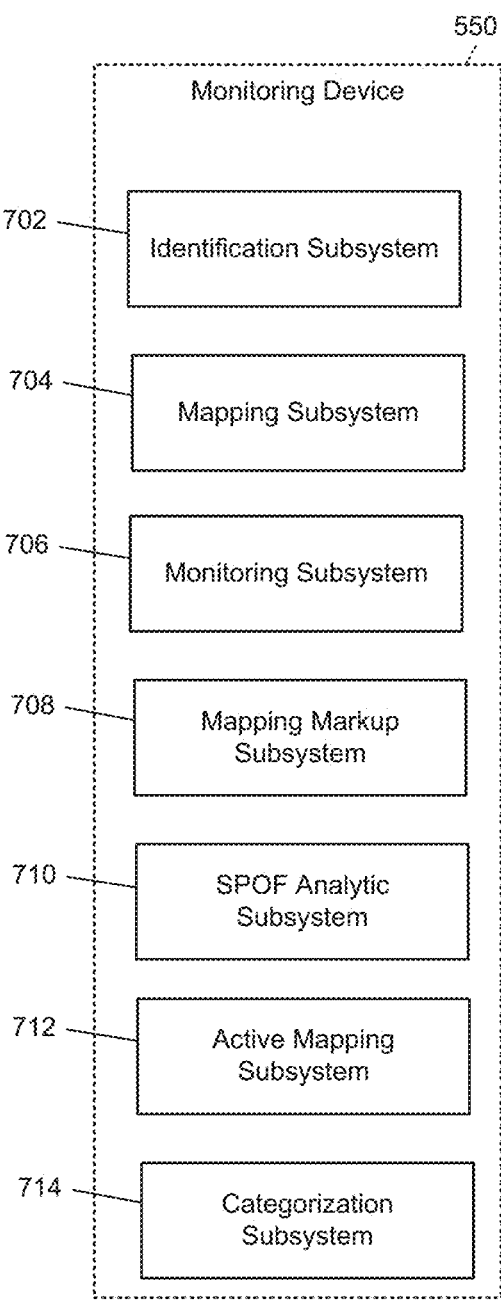
FIG. 7 is a diagram of elements of one or more example computing devices that may be used in the system shown in FIGS. 1-5.

FIG. 7 is a diagram of elements of one or more example computing devices that may be used in the system shown in FIGS. 1-5. As described herein, the elements 702, 704, 706, 708, 710, 712, and 714 are configured to perform the processes and methods described herein. Identification subsystem 702 is configured to perform the identification tasks described herein related to identifying components and assets in the ecosystem, their characteristics, and their relationships and connectivity. Mapping subsystem 704 is configured to generate a topological map based on information identified by identification subsystem 702. Monitoring subsystem 706 is configured to perform the steps of monitoring the assets of the ecosystem as described herein. Mapping markup subsystem 708 is configured to provide the annotations and multi-layered contextual information applied to the topological ecosystem map as described herein. Single point of failure analytic subsystem 710 is configured to identify points of failure within the ecosystem where a host is non-redundant with any other host, and may present a risk of SPOF for a given service. Active mapping subsystem 712 is configured to provide an active map generated based on information received from monitoring the ecosystem and the topological map. Categorization subsystem 714 is group or categorize the assets of the ecosystem according to their characteristics including, for example, their cluster designations, tiers, location, or asset type and manufacturer.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A system for mapping and monitoring inter-application communications in a computing ecosystem, the system comprising:

a plurality of host devices having corresponding host processors and corresponding host memory devices, wherein the corresponding host processors execute corresponding host applications; and a monitoring device including a processor and a memory device, wherein the monitoring device is in networked communication with the plurality of host devices via a network, wherein the processor is configured to:

identify a plurality of communication paths linking the plurality of host devices, wherein each of the plurality of communication paths provides for inter-application communications between the host applications;

generate an ecosystem map that depicts the plurality of host devices and the plurality of communication paths;

transmit a monitoring signal to obtain monitoring responses from the plurality of host devices via the network;

receive monitoring responses in response to the monitoring signal, the monitoring responses providing status information of the host applications including at least a first status providing data on health of at least one of the plurality of host devices, a condition of at least one of the host applications, or both;

process the monitoring responses with the ecosystem map to generate an active ecosystem map that includes the status information of each of the host applications; and display the active ecosystem map to provide a central view of the inter-application communications between the host applications in the computing ecosystem, wherein the central view provides a single point of display for review and management of the computing ecosystem based on the status information of each of the host applications.

2. The system of claim 1, wherein the processor is further configured to perform indirect monitoring of the plurality of host devices by:

transmitting the monitoring signal to at least one external monitoring device that actively polls the plurality of host devices; and receiving the monitoring responses from the at least one external monitoring device.

3. The system of claim 1, wherein the processor is further configured to perform direct monitoring of the plurality of host devices by:

transmitting the monitoring signal to the plurality of host devices; and receiving the monitoring responses from the plurality of host devices.

4. The system of claim 1, wherein the processor is further configured to:

identify the plurality of host devices by sending an inquiry message to the network; and generate the ecosystem map based on the identified host devices and the communication paths linking the plurality of host devices.

5. The system of claim 1, wherein the processor is further configured to:

group the plurality of host devices into a plurality of logical groupings based on at least one of a host tier model and a host cluster model; and display the active ecosystem map including the plurality of host devices grouped by the logical groupings.

6. The system of claim 1, wherein the processor is further configured to:

display the active ecosystem map including a first layer representing a topological depiction of the plurality of host devices and a second layer representing a set of information associated with the plurality of host devices.

7. The system of claim 1, wherein the processor is further configured to:

group the plurality of host devices into a plurality of logical groupings based on a host cluster model;

identify a non-redundant host device supporting at least one of the logical groupings;

designate the non-redundant host device as a point-of-failure; and transmit an alert regarding the designated point-of-failure.

8. A device for mapping and monitoring inter-application communications in a computing ecosystem, the device including a processor and a memory device, wherein the device is in networked communication via a network with a plurality of host devices having corresponding host processors and corresponding host memory devices, wherein the corresponding host processors execute corresponding host applications, and wherein the processor is configured to:

identify a plurality of communication paths linking the plurality of host devices, wherein each of the communication paths provides for inter-application communications between the host applications;

generate an ecosystem map that depicts the plurality of host devices and the plurality of communication paths;

transmit a monitoring signal to obtain monitoring responses from the plurality of host devices via the network;

receive monitoring responses in response to the monitoring signal, the monitoring responses providing status information of the host applications including at least a first status providing data on health of at least one of the plurality of host devices, a condition of at least one of the host applications, or both;

process the monitoring responses with the ecosystem map to generate an active ecosystem map that includes the status information of each of the host applications; and display the active ecosystem map to provide a central view of the inter-application communications between the host applications in the computing ecosystem, wherein the central view provides a single point of display for review and management of the computing ecosystem based on the status information of each of the host applications.

9. The device of claim 8, wherein the processor is further configured to perform indirect monitoring of the plurality of host devices by:

transmitting the monitoring signal to at least one external monitoring device that actively polls the plurality of host devices; and receiving the monitoring responses from the at least one external monitoring device.

10. The device of claim 8, wherein the processor is further configured to perform direct monitoring of the plurality of host devices by:

transmitting the monitoring signal to the plurality of host devices; and receiving the monitoring responses from the plurality of host devices.

11. The device of claim 8, wherein the processor is further configured to:

display the active ecosystem map including a first layer representing a topological depiction of the plurality of host devices and a second layer representing a set of information associated with the plurality of host devices.

12. The device of claim 8, wherein the processor is further configured to:

group the plurality of host devices into a plurality of logical groupings based on a host cluster model;

identify a non-redundant host device supporting at least one of the logical groupings;

designate the non-redundant host device as a point-of-failure; and transmit an alert regarding the designated point-of-failure.

13. The device of claim 8, wherein the processor is further configured to:

identify the plurality of host devices by sending an inquiry message to the network; and generate the ecosystem map based on the identified host devices and the communication paths linking the plurality of host devices.

14. The device of claim 8, wherein the processor is further configured to:

group the plurality of host devices into a plurality of logical groupings based on at least one of a host tier model and a host cluster model; and display the active ecosystem map including the plurality of host devices grouped by the logical groupings.

15. A method for mapping and monitoring inter-application communications in a computing ecosystem, wherein the method is performed by a monitoring device including a processor and a memory device, wherein the monitoring device is in networked communication with a plurality of host devices having corresponding host processors and corresponding host memory devices, wherein the corresponding host processors execute corresponding host applications, the method comprising:

identifying a plurality of communication paths linking the plurality of host devices, wherein each of the communication paths provides for inter-application communications between the host applications;

generating an ecosystem map that depicts the plurality of host devices and the plurality of communication paths;

transmitting a monitoring signal to obtain monitoring responses from the plurality of host devices via the network;

receiving monitoring responses in response to the monitoring signal, the monitoring responses providing status information of the host applications including at least a first status providing data on health of at least one of the plurality of host devices, a condition of at least one of the host applications, or both;

processing the monitoring responses with the ecosystem map to generate an active ecosystem map that includes the status information of each of the host applications; and displaying the active ecosystem map to provide a central view of the inter-application communications between the host applications in the computing ecosystem, wherein the central view provides a single point of display for review and management of the computing ecosystem based on the status information of each of the host applications.

16. The method of claim 15, further comprising performing indirect monitoring of the plurality of host devices by:

transmitting the monitoring signal to at least one external monitoring device that actively polls the plurality of host devices; and receiving the monitoring responses from the at least one external monitoring device.

17. The method of claim 15, further comprising performing direct monitoring of the plurality of host devices by:

transmitting the monitoring signal to the plurality of host devices; and receiving the monitoring responses from the plurality of host devices.

18. The method of claim 15, further comprising:

displaying the active ecosystem map including a topological mapping tool;

receiving an input at the topological mapping tool; and displaying the active ecosystem map with a first layer generated based on the input.

19. The method of claim 15, further comprising:

grouping the plurality of host devices into a plurality of logical groupings based on a host cluster model;

identifying a non-redundant host device supporting at least one of the logical groupings;

designating the non-redundant host device as a point-of-failure; and transmitting an alert regarding the designated point-of-failure.

20. The method of claim 15, further comprising:

performing a correlation between the monitoring responses; and generating the active ecosystem map based on the correlation.

* * * * *